United States Patent [19]

Rentzea et al.

[11] 4,327,214

[45] Apr. 27, 1982

[54] SUBSTITUTED ALKYLAMMONIUM SALTS, THE MANUFACTURE THEREOF, THE USE THEREOF FOR REGULATING PLANT GROWTH, AND AGENTS THEREFOR

[75] Inventors: Costin Rentzea, Heidelberg; Hubert Sauter, Mannheim; Johann Jüng, Limburgerhof, all of Fed. Rep. of Germany

[73] Assignee: BASF Aktiengesellschaft, Fed. Rep. of Germany

[21] Appl. No.: 186,602

[22] Filed: Sep. 12, 1980

[30] Foreign Application Priority Data

Oct. 8, 1979 [DE] Fed. Rep. of Germany ....... 2940765

[51] Int. Cl.³ .................. C07D 487/04; C07D 453/02
[52] U.S. Cl. ............................. 546/133; 260/326.5 B; 260/326.5 S; 260/326.5 M; 260/326.5 J; 544/158; 544/174; 564/341; 564/352; 71/94; 71/95; 71/98; 71/121
[58] Field of Search ................. 546/133; 260/326.5 B, 260/326.5 S

[56] References Cited

U.S. PATENT DOCUMENTS

| | | | |
|---|---|---|---|
| 3,156,554 | 11/1964 | Talbert | 71/2.7 |
| 3,875,215 | 4/1975 | Strycker | 546/133 |
| 4,196,143 | 4/1980 | Strycker | 546/133 |

FOREIGN PATENT DOCUMENTS 2017497  4/1970  Fed. Rep. of Germany.
1310372  3/1973  United Kingdom.

OTHER PUBLICATIONS

J. Org. Chem. 17 (1952), pp. 693–697.
Helv. Chim. Acta 54 (1971), pp. 112–117.
K. H. Konig, Naturwissenschaften, vol. 55 (1968), pp. 217–219.

*Primary Examiner*—Norma S. Milestone
*Attorney, Agent, or Firm*—Keil & Witherspoon

[57] ABSTRACT

Substituted alkylammonium salts of the formula

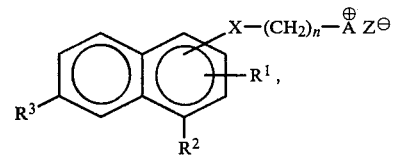

where $R^1$, $R^2$ and $R^3$ are hydrogen, $C_{1-4}$-alkyl, fluorine, chlorine or bromine, X is oxygen or sulfur, n denotes one of the integers 2, 3 and 4, A denotes quinuclidine or pyrrolizidine, or $-NR^4R^5R^6$, $R^4$, $R^5$ and $R^6$ denoting $C_{1-6}$-alkyl, $C_{2-6}$-alkenyl or $C_{2-6}$-alkynyl which are unsubstituted or substituted by halogen, cyano or $C_{1-4}$-alkoxy, or $R^5$ and $R^6$, as alkylene groups, may be part of an unsubstituted or $C_{1-2}$-alkyl-substituted 5- or 6-membered heterocycle with 1 to 3 heteroatoms in the ring, and Z is the anion of any non-phytotoxic acid HZ, the manufacture of such compounds, agents for regulating plant growth containing these compounds, and the use thereof for regulating plant growth.

4 Claims, No Drawings

SUBSTITUTED ALKYLAMMONIUM SALTS, THE MANUFACTURE THEREOF, THE USE THEREOF FOR REGULATING PLANT GROWTH, AND AGENTS THEREFOR

The present invention relates to new, substituted alkylammonium salts, processes for manufacturing these new compounds, and the use of these compounds and agents containing them for regulating plant growth.

The use of quaternary ammonium compounds, such as chlorocholine (CCC, U.S. Pat. No. 3,156,554) or 1-(β-chloroethyl)-1,1-dimethylhydrazinium chloride (CMH, Naturwissenschaften, 55, 217, 1968) for regulating plant growth has been disclosed. However, their action, particulaly, at low application rates, is not always satisfactory and does not always meet the requirements placed on them in practice.

It has further been disclosed (German Laid-Open Application DE-OS No. 2,017,497) that certain quaternary phenoxyethylammonium salts whose hydrogen is, however, not part of a heterocycle, may be used for influencing plant growth. However, their action too, especially at low concentrations, is not always satisfactory.

The object of the invention is to provide substituted alkylammonium salts of the formula

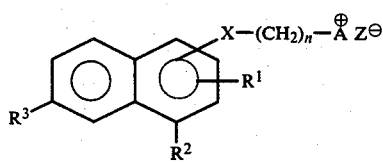

where $R^1$, $R^2$ and $R^3$ are identical or different and each denotes hydrogen, $C_{1-4}$-alkyl, fluorine, chlorine or bromine, X is oxygen or sulfur, n denotes one of the integers 2, 3 and 4, A denotes quinuclidine or pyrrolizidine, or $-NR^4R^5R^6$, $R^4$, $R^5$ and $R^6$ being identical or different and each denoting $C_{1-6}$-alkyl, $C_{2-6}$-alkenyl or $C_{2-6}$-alkynyl which are unsubstituted of substituted by halogen, cyano or $C_{1-4}$-alkoxy, or $R^5$ and $R^6$, as alkylene groups, may be part of an unsubstituted or $C_{1-2}$-alkyl-substituted 5- or 6-membered heterocycle with 1 to 3 heteroatoms in the ring, and Z is the anion of any non-phytotoxic acid HZ.

Preferred compounds of the formula I are those in which the radical $X-(CH_2)_n-A^\oplus Z^\ominus$ is either in the 1- or the 2-position of the naphthalene and X denotes oxygen, and in which $R^1$, $R^2$ and $R^3$ denote hydrogen, methyl or bromine and n is 2.

In a further group of preferred compounds of the formula I, A denotes a trimethyl, triethyl, tripropyl, tributylamine or pyrrolizidine radical, or a pyrrolidine, piperidine or morpholine ring substituted on the quaternary nitrogen by $R^4$.

Preferred radicals for $R^4$ are methyl, ethyl, propyl, butyl, allyl, propargyl, 2-chloroethyl, 2-bromoethyl and 2-buten-1-yl.

As the effectiveness of the compounds of the formula I according to the invention is attributable to the cation, the anion $Z^\ominus$ may be of any non-phytotoxic acid. Examples of meanings for Z are methylsulfonate, p-dodecylbenzenesulfonate, sulfate, methosulfate, nitrate, phosphate, iodide, and especially chloride and bromide.

A further object of the invention is to provide a process for the manufacture of substituted alkylammonium salts of the formula I, wherein (a) a compound of the formula

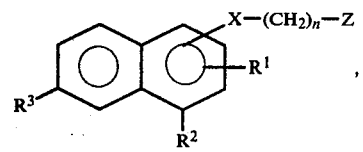

where $R^1$, $R_2$, $R^3$, X, Z and n have the above meanings, is reacted with a tertiary amine of the formula

A                                        III,

A having the above meanings, or (b) a compound of the formula

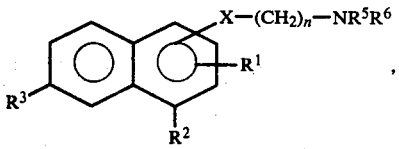

where $R^1$, $R^2$, $R^3$, $R^5$, $R^6$, X and n have the above meanings, is reacted with an alkylating agent of the formula $R^4-Z$                                   V, where $R^4$ and Z have the above meanings.

Reactions (a) and (b) are carried out at from 20° to 150° C., preferably from 50° to 120° C., and in the presence or absence of a solvent or diluent. Examples of preferred solvents or diluents inert to the reactions are aliphatic or aromatic hydrocarbons, such as pentene, cyclohexane, benzene, toluene and xylene; halohydrocarbons, such as chlorobenzene or dichlorobenzenes; ketones, such as acetone, methyl ethyl ketone, diethyl ketone and cyclopentanone; ethers, such as diethyl ether, dimethoxyethane, tetrahydrofuran or dioxane; esters, such as ethyl acetate; nitriles, such as acetonitrile; amides, such as dimethylformamide, dimethylacetamide and N-methylpyrrolidone; or mixtures thereof.

The compounds of the formula II may easily be prepared by prior art processes, for example by etherification of 1- and 2-naphthols or 1- and 2-thionaphthols with aliphatic dihalides, such as 1,2-dibromoethane, 1,3-dibromopropane, 1-chloro-3-bromopropane or 1,4-dibromobutane, preferably in boiling methyl ethyl ketone, diethyl ketone or cyclopentanone in the presence of at least equivalent amounts of potassium carbonate (cf. Houben-Weyl, Methoden der Organischen Chemie, 6/3, 54–59, Thieme-Verlag, Stuttgart, 1965).

Examples of tertiary amines of the formula III which may be used are trimethylamine, triethylamine, tripropylamine, tributylamine, N-methylpyrrolidone, N-ethylpyrrolidone, N-allylpyrrolidone, N-propylpyrrolidone, N-butylpyrrolidone, N-methylpiperidine, N-ethylpiperidine, N-ethylmorpholine, quinuclidine and pyrrolizidine.

The tertiary amines of the formula IV may readily be prepared by known processes, for example in accordance with the scheme

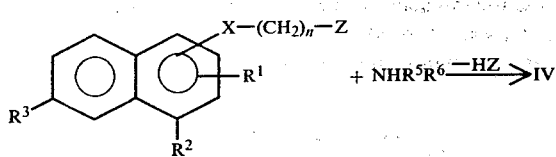

II    VI by alkylation of secondary amines of the formula VI, $R^5$ and $R^6$ having the above meanings, with compounds of the formula II. The reaction conditions are the same as those for the reaction of II+III→I, a 2- to 10-fold molar excess of the amine of the formula VI being preferred here. The HZ formed during the reaction may be easily removed for example by treating the reaction mixture with aqueous alkali metal hydroxides.

Examples of amines of the formula VI which may be employed are diethylamine, dipropylamine, dibutylamine, pyrrolidone, 2-methylpiperidine, 3-methylpiperidine, 4-methylpiperidine, morpholine and 2,6-dimethylmorpholine.

Examples of alkylating agents of the formula V are methyl chloride, methyl bromide, methyl iodide, dimethyl sulfate, ethyl chloride, ethyl iodide, diethyl sulfate, propyl bromide, propyl iodide, allyl chloride, allyl bromide, butyl bromide, butyl chloride, propargyl chloride, chloroacetone and chloroacetonitrile.

For the manufacture of starting compounds of the formulae II and IV, for instance the following naphthols and thionaphthols may be used:

1-naphthol, 2-methyl-1-naphthol, 4-methyl-1-naphthol, 4-chloro-1-naphthol, 4-bromo-1-naphthol, 2-chloro-4-methyl-1-naphthol, 2-bromo-4-methyl-1-naphthol, 4-chloro-2-methyl-1-naphthol, 4-bromo-2-methyl-1-naphthol, 2,4-dichloro-1-naphthol, 2,4-dimethyl-1-naphthol, 2-naphthol, 1-chloro-2-naphthol, 1-bromo-2-naphthol, 6-bromo-2-naphthol and 1,6-dichloro-2-naphthol.

The following examples illustrate the preparation of the new compounds of the formula I and the intermediates of the formulae II and IV required for their manufacture.

EXAMPLE 1

(a) Manufacture of the starting material 50.2 g (0.2 mole) of 1-bromo-2-(2-naphthyloxy)-ethane, 200 ml of anhydrous dioxane and 68 (0.8 mole) of piperidine are stirred for 12 hours at 60° C., cooled and then concentrated under reduced pressure. The residue is distributed between 150 ml of water and 300 ml of ether; while cooling with ice, 100 ml of 50% strength sodium hydroxide solution is then added. The ether layer is separated, washed with 100 ml of water, dried and concentrated under reduced pressure. The solid residue is stirred with 50 ml of pentane for 20 minutes at +10° C., filtered and washed with 20 ml of cold pentane. There is obtained 44 g (86.2% of theory) of N-2-(2-naphthyloxy)-ethylpiperidine as colorless crystals; m.p. 49°–51° C.

(b) Manufacture of the end product

A solution of 15.3 g (0.06 mole) of N-2-(2-naphthyloxy)-ethylpiperidine and 24.4 g (0.2 mole) of allyl bromide in 30 ml of anhydrous dioxane and 30 ml of anhydrous acetonitrile is stirred for 24 hours at 60° C. After the solvent and excess allyl bromide have been removed under reduced pressure, the solid residue is stirred for 20 minutes with 50 ml of anhydrous ether and the crystalline precipitate is separated by suction filtration. There is obtained 18.1 g (80% of theory) of N-allyl-N-2-(2-naphthyloxy)-ethylpiperidinium bromide as white crystals; m.p.: 156°–158° C.

EXAMPLE 2

(a) Manufacture of the starting material

A mixture of 144 g (1 mole) of 2-naphthol, 600 ml of diethyl ketone, 275 g (2 moles) of potassium carbonate and 850 g (4.5 moles) of 1,2-dibromoethane is refluxed for 48 hours. Diethyl ketone and excess dibromoethane are then distilled off under reduced pressure and the residue is taken up in 500 ml of methylene chloride and 200 ml of 10% strength sodium hydroxide solution. After the aqueous phase has been separated off, the organic layer is washed with 100 ml of water, dried over sodium sulfate and concentrated under reduced pressure. The solid residue is stirred with 100 ml of n-pentane for 10 minutes at −5° C., filtered and washed with 50 ml of cold pentane. There is obtained 195 g (78% of theory) of pure 1-bromo-2-(2-naphthyloxy)-ethane; m.p.: 93°–95° C.

(b) Manufacture of the end product

A solution of 15.3 g (0.06 mole) of 1-bromo-2-(2-naphthyloxy)ethane and 7 g (0.07 mole) of N-methylpiperidine in 30 ml of dioxane and 30 ml of acetonitrile is stirred for 16 hours at 70° C. After the solution has cooled to +10° C., the white precipitate which has formed is separated by filtration, washed with 30 ml of ether and then with 50 ml of pentane, and dried. There is obtained 13.6 g (64.8% of theory) of N-methyl-N-2-(2-naphthyloxy)-ethylpiperidinium bromide; m.p.: 179°–181° C.

The following compounds of the formula I, the structure of which was confirmed by $^1$H-nuclear resonance and infrared spectra, were obtained analogously to Examples 1 and 2:

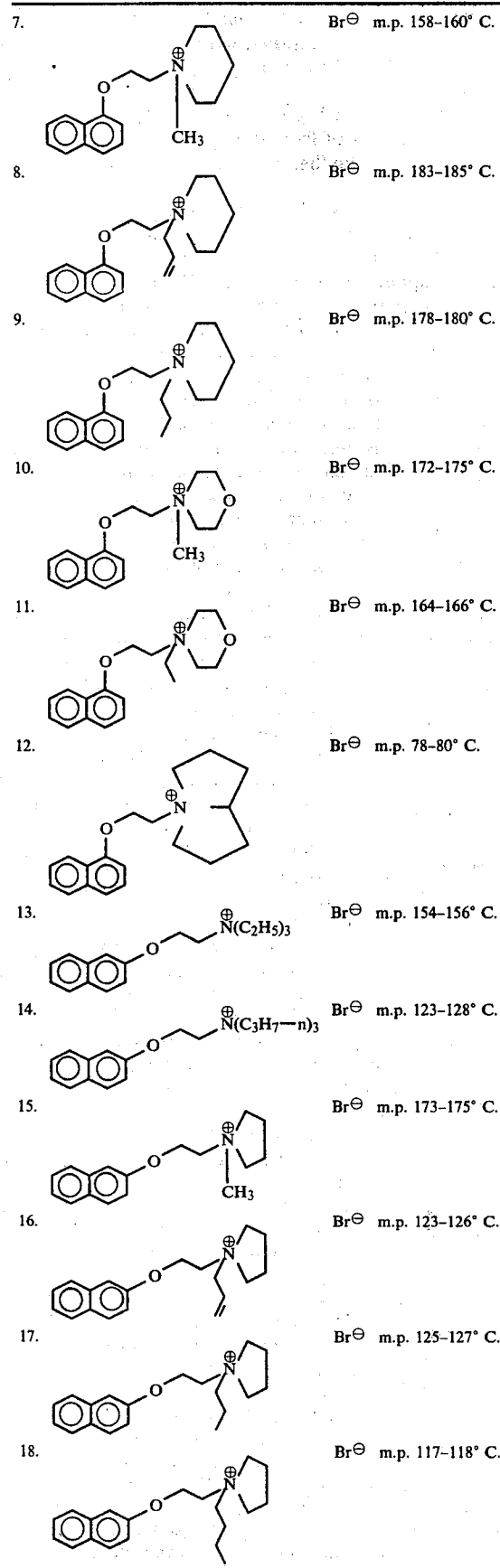
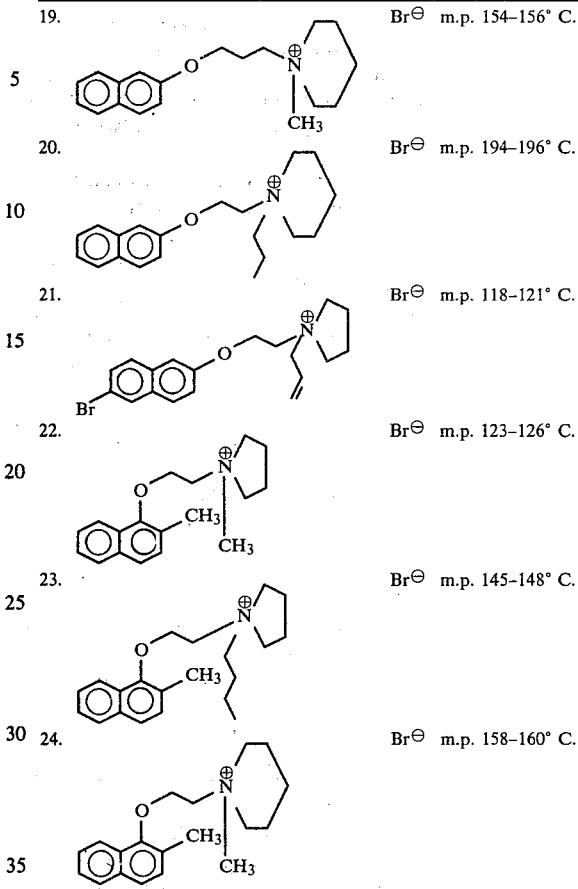

The active ingredients influence plant metabolism and are therefore suitable as growth regulators.

Plant growth regulators may have several different effects on plants.

The diversity of action of growth regulators depends especially on (a) the type and variety of plant;
(b) the time applied, with reference to the development stage of the plants and the time of year;
(c) the place and method of application (seed treatment, soil treatment, or application to leaves);
(d) climatic factors (sunshine duration, average temperature, precipitate);
(e) soil conditions (including fertilization);
(f) the formulation or application form of the active ingredient; and
(g) the concentration at which the active ingredient is applied.

At all events, growth regulators influence crop plants in a desired manner.

A description of some of the various possibilities of using growth regulators in agriculture and horticulture is given below.

A. With the compounds according to the invention, vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn and soybeans. The shortening and strengthening of the stem thus caused reduces or eliminates the danger of lodging under unfavorable weather conditions.

The use of growth regulators is also important for inhibiting plant height and changing the time of ripening in cotton.

It is thus possible for this important crop to be harvested completely mechanically.

Growth regulators may also increase or inhibit lateral branching. This is of inerest when it is desired to inhibit, for instance in tobacco plants, the formation of lateral shoots (suckers) in favor of leaf development.

A further mechanism for increasing yields with plant growth regulators is based on the fact that blossom and fruit formation benefits to a greater extent from the nutrients when vegetative growth is restricted. Further, because of the relatively low leaf or plant mass, attack by various diseases, especially fungus diseases, is prevented.

The inhibition of vegetative growth also makes closer planting possible in numerous crops, which means an increase in yield based on the area cropped. The compounds according to the invention are particularly suitable for inhibiting vegatative plant growth in crop plants such as soybeans, sunflowers, groundnuts, rape, ornamentals, cotton, rice and grasses.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugar beets, sugarcane and citrus fruit, to raise the protein content of cereals and soybeans, and to stimulate the increased formation of latex in rubber trees.

The compounds according to the invention may raise the yield by influencing plant metabolism or by promoting or inhibiting vegetative and/or generative growth.

C. Finally, it is also possible with growth regulators to shorten or lengthen growth stages and to accelerate or retard the ripening process in plant parts either before or after harvesting.

A factor of economical interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also responsible for a chemically induced, readily controllable defloliation of plants.

The action of the compounds according to the invention is superior to that of prior art growth regulators. This action is manifested not only in monocotyledon crops, e.g., cereals such as wheat, barley, rye, oats and rice or Indian corn, or grasses, but also especially in dicotyledons (e.g., sunflowers, tomatoes, ground-nuts, grapes, cotton, rape, and, particularly, soybeans) and various ornamentals such as chrysanthemums, poinsettias and hibiscus.

The compounds according to the invention may be applied to the crop either by treating the seed, treating the soil, i.e., through the roots, or—the mode particularly preferred—by spraying the leaves. Because the active ingredients are well tolerated by the crop plants, application rates may vary within a wide range.

When the active ingredients are used to treat seed, active ingredient amounts of from 0.001 to 50 g, preferably from 0.01 to 10 g, per kg of seed are generally required.

When the active ingredients are applied to the soil or foliage, amounts of from 0.001 to 12 kg/ha, preferably from 0.01 to 3 kg/ha, are generally considered to be sufficient.

The compounds of the invention can be applied in conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines, e.g. ethanolamine and dimethylformamide, and water; carriers, for example natural rock powders, e.g. kaolin, alumina, talc and chalk, and synthetic rock powders, e.g. highly disperse silica silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose. It is preferred to use the compounds according to the invention in aqueous solution, if desired with the addition of water-miscible organic solvents such as methanol or other lower alcohols, acetone, dimethylformamide or N-methylpyrrolidine. The formulations generally contain from 0.1 to 95, and preferably from 0.5 to 90, wt% of active ingredient.

The formulations, and the ready-to-use preparations obtained therefrom, e.g. solutions, emulsions, suspensions, powders, dusts, pastes or granules, are applied in the conventional manner, e.g. preemergence, postemergence, or as seed disinfectants.

Examples of such formulations are given below.

I. 20 parts by weight of the compound of Example 1 is well mixed with 3 parts by weight of the sodium salt of diisobutylnaphthalene-$\alpha$-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

II. 3 parts by weight of the compound of Example 4 is intimately mixed with 97 parts by weight of particulate kaolin. A dust is obtained containing 3% by weight of the active ingredient.

III. 30 parts by weight of the compound of Example 5 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 40 parts by weight of the compound of Example 4 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

V. 20 parts of the compound of Example 6 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

VI. 90 parts by weight of the compound of Example 3 is mixed with 10 parts by weight of N-methyl-α-pyrrolidone. A mixture is obtained which is suitable for application in the form of very fine drops.

VII. 20 parts by weight of the compound of Example 8 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts b yweight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

VIII. 20 parts by weight of the compound of Example 16 is dissolved in a mixture consisting of 40 parts by weight of cyclohexanone, 30 parts by weight of isobutanol, 20 parts of weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IX. 10 parts by weight of the compound of Example 17, 20 parts by weight of polyoxyethylene sorbitan monolaurate ($^R$TWEEN 20), 20 parts by weight of methanol and 50 parts by weight of water are stirred to give a solution containing 10 wt% of the active ingredient. More dilute solutions may be prepared by adding more water.

The agents according to the invention may, in these application forms, also be mixed and applied with other active ingredients, e.g., herbicides, insecticides, other growth regulators, bactericides, fungicides and fertilizers. When mixed with other growth regulators, the spectrum of action is in many cases increased; with a number of these compositions, synergistic effects also occur; i.e., the action of the combination product is greater than the effect of the individual components added together.

Examples of fungicides which can be combined with the compounds of the invention are: dithiocarbamates and their derivatives, e.g. iron(III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfate, the ammonia complex of zinc N,N-ethylene-bis-dithiocarbamate and N,N'-polyethylene-bis (thiocarbamoyl)-disulfide, zinc N,N'-propylene-bis-dithiocarbamate, and the ammonia complex of zinc N,N'-propylene-bis-dithiocarbamate and N,N'-polypropylene-bis-(thiocarbamoyl)-disulfide; nitrophenol derivatives, e.g. dinitro-(1-methylheptyl)-phenyl crotonate, 2sec.-butyl-4,6-dinitrophenyl 3,3-dimethylacrylate and 2-sec.-butyl-4,6-dinitrophenyl isopropyl carbonate; heterocyclic compunds, e.g. N-trichloromethylthiotetrahydrophthalimide, N-trichloromethylthio-phthalimide, 2-heptadecyl-2-imidazole acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazolecarbamate, 2-methoxycarbonylamino-benzimidazole, 2-thiocyanatomethylthio-benzthiazole, 4-(2-chlorophenyl-hydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxyanilido-6-methyl-1,4-oxathiine, 2-fur-2-yl-benzijidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, D,L-methyl-N-(2,6-dimethylphenyl)-N-fur-2-yl-alaninate, methyl D,L-N-(2,6-dimethylphenyl)-N-(2'-methoxyacetyl)-alaninate, diisopropyl 5-nitroisophthalate, 2,5-dimethyl-furan-3-carboxylic acid anilide, 2,5-dimethylfuran-3-carboxylic acid cyclohexylamide, 2-methyl-benzoic acid anilide, 1-(3,4-dichloroanilino)-1-formylamino-2,2,2-trichloroethane, 2,6-dimethyl-N-tridecylmorpholine and its salts, 2,6-dimethyl-N-cyclodoecyl-morpholine and its salts, 2,3-dichloro-1,4-naphthoquinone, 1,4-dichloro-2,5-dimethoxybenzene, p-dimethylaminobenzene diazosodium sulfonate, 1-chloro-2-nitropropane, polychloronitrobenzenes such as pentachloronitrobenzene, methyl isocyanate, fungicidal antibiotics such as griseofulvin or kasugamycin, tetrafluorodichloroacetone, 1-phenyl-thiosemicarbazide, Bordeaux mixture, nickel-containing compounds and sulfur.

The following Example A demonstrates the action of the compounds according to the invention as growth regulators; however, further applications as growth regulators are not excluded.

EXAMPLE A, greenhouse experiment

Plastic pots about 12.5 cm in diameter were filled with a peat substrate provided with sufficient nutrients, and test plants grown therein. In postemergence treatment, the plants were sprayed with aqueous formulations of the substances to be tested. The growth-regulating action observed was confirmed at the end of the experiment by weight measurement. The values obtained were compared with those for untreated plants. The comparative agent employed was CCC:

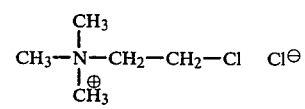

Not only was growth height reduced—the leaves also took on a more intense color. The increased chlorophyll content is indicative of a higher rate of photosynthesis, making for bigger yields.

The individual data are given in the table below.

TABLE

Influence on the growth height of "SRF 450" soybeans
Postemergence treatment; duration of expt.: 25 days

| Compound from Ex. no. | mg of active ingredient per vessel | Growth height cm | % |
|---|---|---|---|
| — | — | 24.8 | 100 |
| CCC | 1.5 | 21.5 | 86.7 |
|  | 6 | 19.5 | 78.6 |
| 1 | 1.5 | 18.0 | 72.6 |
|  | 6 | 18.0 | 72.6 |
| 4 | 1.5 | 18.0 | 72.6 |
|  | 6 | 16.5 | 66.5 |
| 5 | 1.5 | 17.5 | 70.6 |
|  | 6 | 14.5 | 58.5 |
| 9 | 1.5 | 21.0 | 84.7 |
|  | 6 | 19.0 | 76.6 |
| 15 | 1.5 | 20.0 | 80.7 |
|  | 6 | 19.0 | 76.6 |
| 16 | 1.5 | 17.5 | 70.6 |
|  | 6 | 16.0 | 64.5 |
| 17 | 1.5 | 15.0 | 60.5 |
|  | 6 | 14.0 | 56.5 |

We claim:

1. A substituted alkylammonium salt of the formula

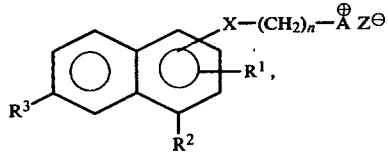

where $R^1$, $R^2$ and $R^3$ are identical or different and each denotes hydrogen, $C_{1-4}$-alkyl, fluorine, chlorine or bromine, X is oxygen or sulfur, n denotes one of the integers 2, 3 and 4, A denotes quinuclidine or pyrrolizidine, and Z is the anion of any non-phytotoxic acid HZ.

2. A compound as set forth in claim 1 wherein A denotes quinuclidine.

3. A compound as set forth in claim 1 wherein A is pyrrolizidine.

4. The compound of claim 2 which is N-2-(1-naphthyloxy)-ethylpyrrolizidinium bromide.

* * * * *